United States Patent [19]
Wood et al.

[11] Patent Number: 6,087,498
[45] Date of Patent: *Jul. 11, 2000

[54] PROCESS FOR THE PREPARATION OF UNSYMMETRICAL 4,6-BIS(ARYLOXY) PYRIMIDINE COMPOUNDS

[75] Inventors: William Wakefield Wood, Pennington; Salvatore John Cuccia, Lawrenceville, both of N.J.; Robert Brigance, Levittown, Pa.

[73] Assignee: American Cyanamid Company, Madison, N.J.

[*] Notice: This patent is subject to a terminal disclaimer.

[21] Appl. No.: 09/270,927

[22] Filed: Mar. 16, 1999

Related U.S. Application Data

[62] Division of application No. 09/076,435, May 12, 1998, Pat. No. 5,977,363.
[60] Provisional application No. 60/013,019, Mar. 7, 1996.
[51] Int. Cl.⁷ ........................ C07D 239/52; C07D 239/60
[52] U.S. Cl. .................. 544/299; 544/301; 544/302; 544/303; 544/304; 544/319
[58] Field of Search ................................ 544/319, 299, 544/301, 302, 303, 304

[56] References Cited

U.S. PATENT DOCUMENTS

| | | | |
|---|---|---|---|
| 4,900,352 | 2/1990 | Wada et al. | 544/309 |
| 5,395,837 | 3/1995 | Clough et al. | 544/319 |
| 5,849,910 | 12/1998 | Kameswaran | 544/319 |

FOREIGN PATENT DOCUMENTS

| | | |
|---|---|---|
| 94/02470 | 7/1993 | WIPO . |
| 94/02470 | 2/1994 | WIPO . |
| 95/05367 | 2/1995 | WIPO . |

OTHER PUBLICATIONS

CA 105:42681 (1986).
CA 104: 129865 (1985).

*Primary Examiner*—John M. Ford
*Assistant Examiner*—V Balasubramanian
*Attorney, Agent, or Firm*—Barbara L. Renda

[57] ABSTRACT

There is provided a process for the preparation of unsymmetrical 4,6-bis(aryloxy)pyrimidine compounds. The unsymmetrical 4,6-bis(aryloxy)pyrimidine compounds are useful as pesticidal agents.

11 Claims, No Drawings

PROCESS FOR THE PREPARATION OF UNSYMMETRICAL 4,6-BIS(ARYLOXY) PYRIMIDINE COMPOUNDS

This is a divisional of application Ser. No. 09/076,435 filed on May 12, 1998 which is now a U.S. Pat. No. 5,977,363 which claims benefit of U.S. provisional application No. 60/013,019 filed on Mar. 7, 1996 and the entire disclosure of the application is hereby incorporated by reference.

BACKGROUND OF THE INVENTION

Symmetrical and unsymmetrical 4,6-bis(aryloxy) pyrimidine compounds which are useful as pesticidal agents are described in WO 94/02470. Symmetrical 4,6-bis (aryloxy)pyrimidine compounds are prepared in one step by reacting a 4,6-dihalopyrimidine compound with two molar equivalents of a phenol compound. In contrast, unsymmetrical 4,6-bis(aryloxy)pyrimidine compounds are significantly more difficult to prepare because the aryloxy groups must be introduced by separate reactions.

WO 94/02470 discloses that unsymmetrical 4,6-bis (aryloxy)pyrimidine compounds are prepared by reacting a 4,6-dihalopyrimidine compound with one molar equivalent of a first phenol compound in the presence of a base and then reacting the resulting compound with a second phenol compound in the presence of a base. However, that process is not entirely satisfactory for the commercial manufacture of unsymmetrical 4,6-bis(aryloxy)pyrimidine compounds. When 4,6-dichloropyrimidine is used, scrambling of the aryloxy groups occurs, producing symmetrical compounds which are difficult to separate from the desired unsymmetrical product, as shown in Flow Diagram I.

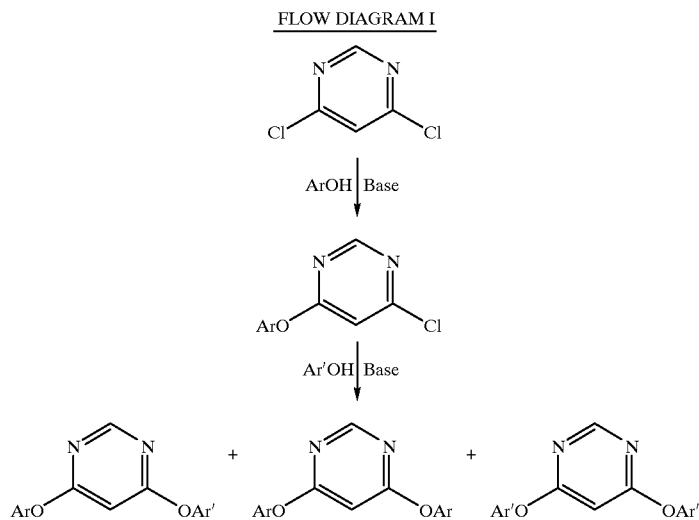

To overcome the scrambling problem associated with the use of 4,6-dichloropyrimidine, 4,6-difluoropyrimidine has been used. However, 4,6-difluoropyrimidine is prepared from 4,6-dichloropyrimidine by a halogen exchange reaction which requires the use of costly reagents and consumes a large amount of energy.

It is therefore an object of the present invention to provide a process for the preparation of unsymmetrical 4,6-bis (aryloxy)pyrimidine compounds which overcomes the problems associated with the processes of the art.

SUMMARY OF THE INVENTION

The present invention relates to a process for the preparation of an unsymmetrical 4,6-bis(aryloxy)pyrimidine compound having the structural formula I

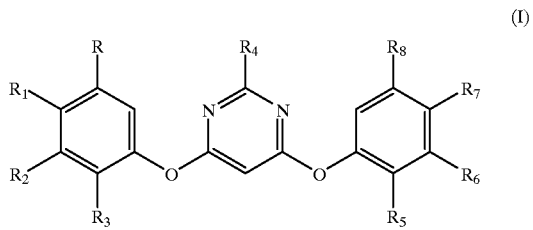

wherein
R and $R_8$ are each independently hydrogen or halogen;
$R_1$ and $R_7$ are each independently hydrogen, halogen, cyano, nitro, alkyl, haloalkyl, alkoxy, alkylthio, amino, alkylamino, dialkylamino, alkoxyalkyl, haloalkoxyalkyl or alkoxycarbonyl;
$R_2$ and $R_6$ are each independently hydrogen, halogen, alkyl, haloalkyl, haloalkoxy, haloalkylthio, haloalkenyl, haloalkynyl, haloalkoxyalkyl, alkoxycarbonyl, haloalkoxycarbonyl, haloalkylsulfinyl, haloalkylsulfonyl, nitro or cyano;
$R_3$ and $R_5$ are each independently hydrogen, halogen, alkyl or alkoxy; and
$R_4$ is hydrogen, cyano, alkyl, haloalkyl, alkoxy, alkylthio, alkylsulfinyl or phenyl;
provided that at least one of $R_2$ and $R_6$ is other than hydrogen, and that the aryloxy groups are not the same; which comprises reacting a 4,6-dihalopyrimidine compound having the structural formula II

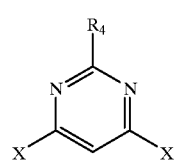

wherein $R_4$ is as described above and X is Cl, Br or I with one molar equivalent or less of a first phenol compound having the structural formula III

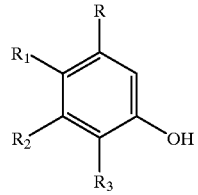
(III)

wherein R, $R_1$, $R_2$ and $R_3$ are as described above and a first base in the presence of a first solvent to form a 4-halo-6-(aryloxy)pyrimidine compound having the structural formula IV

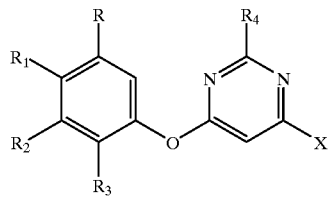
(IV)

wherein R, $R_1$, $R_2$, $R_3$, $R_4$ and X are as described above, reacting the 4-halo-6-(aryloxy)pyrimidine compound with at least about one molar equivalent of a $C_1$–$C_4$trialkylamine, a 5- to 6-membered saturated or 5- to 14-membered unsaturated heterocyclic amine optionally substituted with one to three $C_1$–$C_4$alkyl groups or $C_1$–$C_4$alkoxy groups in the presence of a second solvent to form an ammonium halide compound having the structural formula V

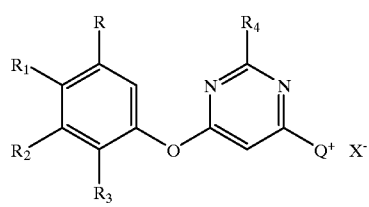
(V)

wherein R, $R_1$, $R_2$, $R_3$, $R_4$ and X are as described above, $Q^+$ is

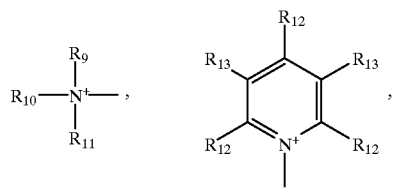

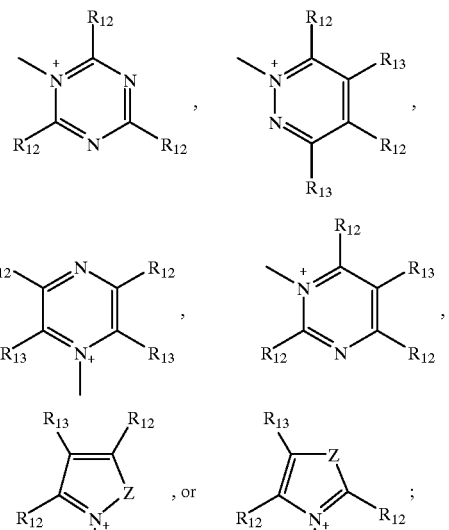

$R_9$, $R_{10}$, and $R_{11}$ are each independently $C_1$–$C_4$alkyl, and when taken together, $R_9$ and $R_{10}$ may form a 5- or 6-membered ring in which $R_9R_{10}$ is represented by the structure: —$(CH_2)_n$—, optionally interrupted by O, S or $NR_{14}$, where n is an integer of 3, 4 or 5, provided $R_{11}$ is $C_1$–$C_4$alkyl;

Z is O, S or $NR_{14}$, $R_{12}$ and $R_{13}$ are each independently hydrogen, $C_1$–$C_4$alkyl or $C_1$–$C_4$alkoxy, and when taken together, $R_{12}$ and $R_{13}$ may form a 5- or 6-membered saturated or unsaturated ring optionally interrupted by O, S or $NR_{14}$ and optionally substituted with one to three $C_1$–$C_4$alkyl groups or $C_1$–$C_4$alkoxy groups; and $R_{14}$ is $C_1$–$C_4$alkyl; and reacting the ammonium halide compound with at least about one molar equivalent of a second phenol compound having the structural formula VI

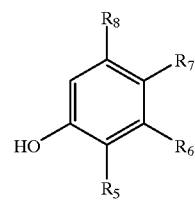
(VI)

wherein $R_5$, $R_6$, $R_7$ and $R_8$ are as described above and a second base in the presence of a third solvent to form the desired formula I compound.

Advantageously, the process of the present invention provides unsymmetrical bis(aryloxy)pyrimidine compounds in higher yield than the art processes, overcomes the scrambling problem associated with the 4,6-dichloropyrimidine art process and uses less costly reagents than the 4,6-difluoropyrimidine art process.

DETAILED DESCRIPTION OF THE INVENTION

The process preferably comprises reacting a formula II 4,6-dihalopyrimidine compound as described above with one molar equivalent of a formula III first phenol compound as described above and at least one molar equivalent of the first base in the presence of the first solvent preferably at a temperature range of about 0° C. to 100° C. to form a formula IV 4-halo-6-(aryloxy)pyrimidine compound as described above, reacting the formula IV compound with at least about one molar equivalent of the amine as described above in the presence of the second solvent preferably at a temperature of about 0° C. to 100° C. to form a formula V ammonium halide compound as described above, and reacting the formula V compound with one molar equivalent of a formula VI second phenol compound and at least about one molar equivalent of the second base in the presence of the third solvent preferably at a temperature of about 0° C. to 100° C. to form the desired unsymmetrical 4,6-bis (aryloxy)pyrimidine compound of formula I. The reaction scheme is shown in Flow Diagram II.

FLOW DIAGRAM II

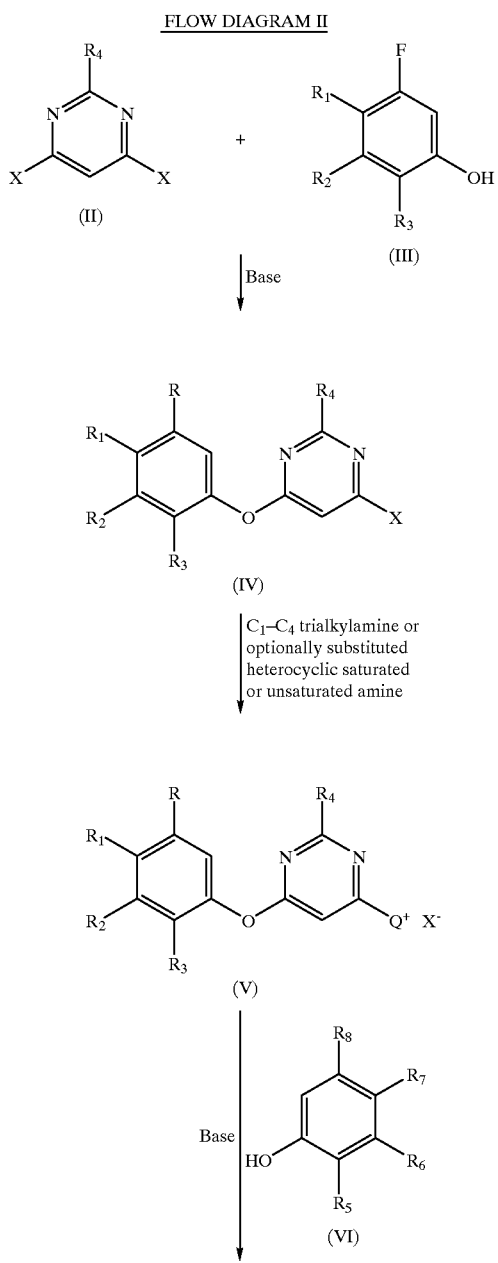

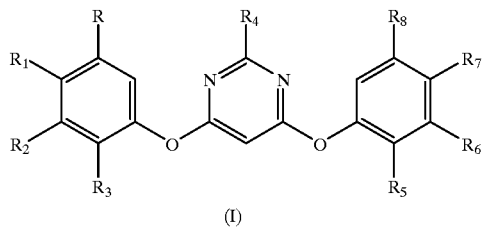

(I)

The unsymmetrical 4,6-bis(aryloxy)pyrimidine compounds may be isolated by diluting the reaction mixture with water and filtering the formula I product from the aqueous mixture. The product formula I compounds may also be isolated by extracting the aqueous mixture with a suitable solvent. Suitable extraction solvents include substantially water-immiscible solvents such as diethyl ether, ethyl acetate, toluene, methylene chloride and the like.

The ammonium halide compounds are an especially important feature of the present invention. When an ammonium halide compound is reacted with a second phenol compound, scrambling of the aryloxy groups does not occur. Surprisingly, disadvantageous scrambling has been overcome by the process of the present invention without requiring the use of 4,6-difluoropyrimidine.

The amines that may be used in the process of the invention to prepare the ammonium halide compounds are alkyl amines, 5- to 6-membered saturated and 5- to 14-membered unsaturated heterocyclic amines optionally substituted with one to three $C_1$–$C_4$alkyl groups or $C_1$–$C_4$alkoxy groups. The preferred amines are $C_1$–$C_4$trialkylamines, 5- or 6-membered saturated heterocyclic amines, and 5- 14-membered unsaturated heterocyclic amines wherein the heterocyclic ring system contains one to three nitrogen atoms and optionally include sulfur or oxygen in the ring system.

The more preferred amines include trimethylamine, the saturated heterocyclic amines including pyridines, picolines, pyrazines, pyridazines, triazines, quinolines, isoquinolines, imidazoles, benzothiazoles and benzimidazoles, optionally substituted with one to three $C_1$–$C_4$alkyl groups or $C_1$–$C_4$alkoxy groups, and unsaturated heterocyclic amines such as pyrrolidines, piperidines, piperazines, morpholines, thiazolidines and thiamorpholines.

First and second bases suitable for use in the process of the present invention include alkali metal carbonates such as sodium carbonate and potassium carbonate, alkaline earth metal carbonates such as calcium carbonate and magnesium carbonate, alkali metal hydrides such as sodium hydride and potassium hydride, alkali metal hydroxides such as sodium hydroxide and potassium hydroxide, and alkaline earth metal hydroxides such as calcium hydroxide and magnesium hydroxide, with alkali metal carbonates being preferred.

First solvents suitable for use include ethers such as diethyl ether, tetrahydrofuran and dioxane, carboxylic acid amides such as N,N-dimethylformamide and N,N-dimethylacetamide, halogenated hydrocarbons such as 1,2-dichloroethane, carbon tetrachloride, methylene chloride and chloroform, sulfoxides such as dimethyl sulfoxide, ketones such as acetone and N-methylpyrrolidone, and mixtures thereof. Second solvents suitable for use in the process of this invention include aromatic hydrocarbons such as toluene, xylenes and benzene, halogenated aromatic hydrocarbons such as chlorobenzene and dichlorobenzenes, and mixtures thereof. Third solvents suitable for use in the invention process include carboxylic acid amides such as N,N-dimethylformamide and N,N-dimethylacetamide, sulfoxides such as dimethyl sulfoxide, and mixtures thereof.

Preferred first solvents include carboxylic acid amides and ketones. Preferred second solvents include aromatic hydrocarbons. And preferred third solvents include carboxylic acid amides.

In formula I above, an alkyl group is suitably a straight chain or branched chain group containing up to 8 carbon atoms, for example up to 6 carbon atoms. Preferably, an alkyl group contains up to 4 carbon atoms. An alkyl moiety which forms part of another group, for example the alkyl of a haloalkyl group or each alkyl of an alkoxyalkyl group, suitably has up to 6 carbon atoms, preferably up to 4 carbon atoms.

In formula I above, halogen is fluorine, chlorine, bromine or iodine. Haloalkyl and haloalkoxy are especially trifluoromethyl, pentafluoroethyl and trifluoromethoxy.

The process of the present invention is especially useful for the preparation of formula I unsymmetrical 4,6-bis(aryloxy)pyrimidine compounds wherein R and $R_8$ are the same and each represents hydrogen or fluorine;

$R_1$ and $R_7$ are each independently hydrogen, halogen, cyano, nitro or $C_1$–$C_4$alkyl;

$R_2$ and $R_6$ are each independently hydrogen, fluorine, chlorine, $C_1$–$C_4$alkyl, $C_1$–$C_4$haloalkyl, $C_1$–$C_4$haloalkoxy, $C_2$–$C_4$haloalkenyl, $C_1$–$C_4$alkoxycarbonyl or nitro;

$R_3$ and $R_5$ are each independently hydrogen, halogen or $C_1$–$C_4$alkyl; and $R_4$ is hydrogen, $C_1$–$C_4$haloalkyl, $C_1$–$C_4$alkylthio, $C_1$–$C_4$alkylsulfinyl or phenyl;

provided that at least one of $R_2$ and $R_6$ is other than hydrogen, and that the aryloxy groups are not the same.

In particular, the process of this invention is used to prepare unsymmetrical 4,6-bis(aryloxy)pyrimidine compounds of formula I wherein R, $R_3$, $R_4$, $R_5$ and $R_6$ are hydrogen;

one of $R_1$ and $R_7$ is hydrogen, chlorine or cyano and the other is fluorine; and $R_2$ and $R_6$ are trifluoromethyl.

In order to facilitate a further understanding of the invention, the following examples are presented to illustrate more specific details thereof. The invention is not to be limited thereby except as defined in the claims.

EXAMPLE 1

Preparation of 4-[(4-Chloro-α,α,α-trifluoro-m-tolyl)oxy]-6-[(α,α,α,4-tetrafluoro-m-tolyl)oxy]pyrimidine—Invention Process a) Preparation of 4-Chloro-6-[(α,α,α,4-tetrafluoro-m-tolyl)oxy]pyrimidine

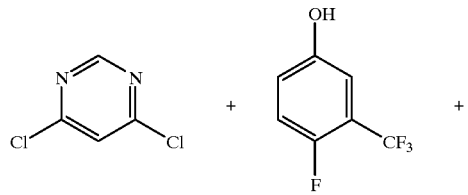

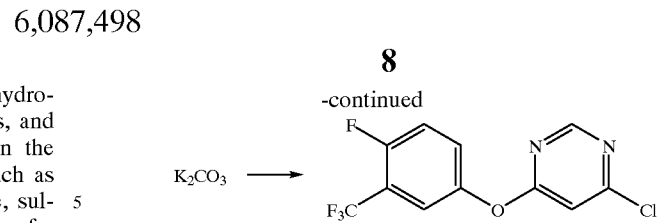

α,α,α,4-Tetrafluoro-m-cresol (1,208.9 g, 6.71 mol) is slowly added to a mixture of 4,6-dichloropyrimidine (1,000.0 g, 6.71 mol) and potassium carbonate (967.5 g, 7.00 mol) in N,N-dimethylformamide (10 L). The reaction mixture is stirred overnight at room temperature, stirred at 45° C. for 2 hours, stirred at 71° C. for 2 hours, stirred overnight at room temperature and poured into water (20 L). The resultant aqueous mixture is extracted with methylene chloride. The organic extracts are combined, washed sequentially with water, 5% sodium hydroxide solution and brine, dried over anhydrous magnesium sulfate and concentrated in vacuo to obtain the title product as a brown oil (1,943.3 g, 99% yield).

b) Preparation of Trimethyl{6-[(α,α,α,4-tetrafluoro-m-tolyl)oxy]-4-pyrimidyl}ammonium chloride

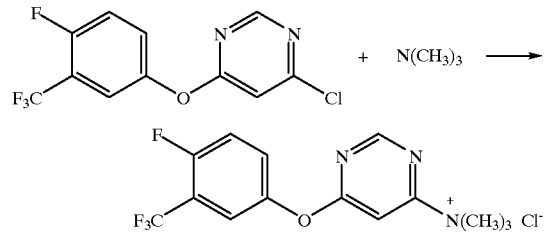

Liquefied trimethylamine (1,255 g, 21.24 mol) is added to a solution of 4-chloro-6-[(α,α,α,4-tetrafluoro-m-tolyl)oxy]pyrimidine (2,038.8 g, 6.97 mol) in toluene (17 L). The reaction mixture is stirred overnight at room temperature and filtered. The resultant solid is washed sequentially with toluene and hexanes and dried overnight in a vacuum oven at 60–65° C. to obtain the title product as a white solid (1,962 g, 80% yield).

c) Preparation of 4-[(4-Chloro-α,α,α-trifluoro-m-tolyl)oxy]-6-[(α,α,α,4-tetrafluoro-m-tolyl)oxy]pyrimidine

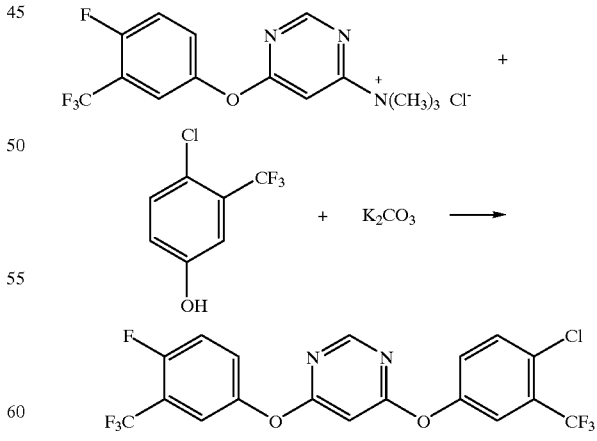

α,α,α-Trifluoro-4-chloro-m-cresol (1,118.9 g, 5.69 mol) is added to a mixture of trimethyl{6-[(α,α,α,4-tetrafluoro-m-tolyl)oxy]-4-pyrimidyl}ammonium chloride (1,962.0 g, 5.58 mol) and potassium carbonate (793.2 g, 5.74 mol) in N,N-dimethylformamide (8.5 L). The reaction mixture is stirred overnight at room temperature, cooled to 5° C. and slowly diluted with water (2.27 L). The resultant aqueous mixture is filtered to give a solid. The solid is washed sequentially with water, hexanes and water, dried overnight in a vacuum oven at 40–45° C. and recrystallized from hexanes to obtain the title product as a yellow solid (1,731.5 g, 69% yield).

As can be seen from the data in Example 1, the title product is prepared in 55% yield starting from 4,6-dichloropyrimidine.

EXAMPLE 2

Preparation of 4-[(4-Chloro-α,α,α-trifluoro-m-tolyl)oxy]-6-[(α,α,α,4-tetrafluoro-m-tolyl)oxy]pyrimidine-4,6-Difluoropyrimidine Art Process a) Preparation of 4,6-Difluoropyrimidine

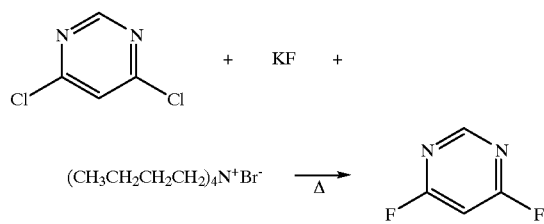

A mixture of 4,6-dichloropyrimidine (223.5 g, 1.5 mol), potassium fluoride (279.6 g, 4.8 mol) and tetrabutylammonium bromide (6.0 g, 0.0186 mol) in sulfolane (1 L) is heated at 180–190° C. for 3.5 hours and distilled to give the title product as a white liquid (115 g, 66% yield).

b) Preparation of 4-[(4-Chloro-α,α,α-trifluoro-m-tolyl)oxy]-6-fluoropyrimidine

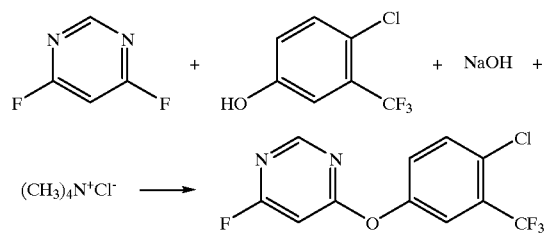

A solution of sodium hydroxide (14.8 g, 0.37 mol) and tetramethylammonium chloride (0.928 g, 0.00847 mol) in water (140 mL) is slowly added to a solution of 4,6-difluoropyrimidine (44 g, 0.379 mol) and α,α,α-trifluoro-4-chloro-m-cresol (72.5 g, 0.369 mol) in methylene chloride (270 mL). The reaction mixture is stirred at room temperature for 2 hours and the phases are separated. The aqueous phase is extracted with methylene chloride and the organic extract is combined with the organic phase. The resultant organic solution is washed with 1N sodium hydroxide solution, dried over anhydrous sodium sulfate and concentrated in vacuo to obtain a solid. The solid is recrystallized from petroleum ether to give the title product as white crystals (73.7 g, 66% yield).

c) Preparation of 4-[(4-Chloro-α,α,α-trifluoro-m-tolyl)oxy]-6-[(α,α,α,4-tetrafluoro-m-tolyl)oxy]pyrimidine

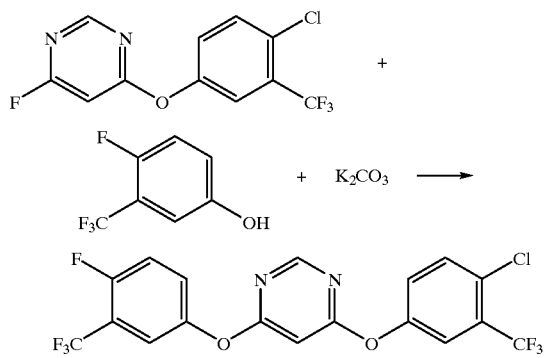

A solution of α,α,α,4-tetrafluoro-m-cresol (59.7 g, 0.33 mol) in N,N-dimethylformamide (150 mL) is added to a mixture of 4-[(4-chloro-α,α,α-trifluoro-m-tolyl)oxy]-6-fluoropyrimidine (97 g, 0.33 mol) and potassium carbonate (91.5 g, 0.66 mol) in N,N-dimethylformamide (200 mL) over a 5 minute period. The reaction mixture is stirred at room temperature for 4.5 hours, treated with additional α,α,α,4-tetrafluoro-m-cresol (6 g), stirred at room temperature for one hour, treated with additional α,α,α,4-tetrafluoro-m-cresol (2 g), stirred overnight at room temperature, treated with additional α,α,α,4-tetrafluoro-m-cresol (1 g), stirred at room temperature for 1 hour and poured into an ice-water mixture (1,780 g). The resultant aqueous mixture is stirred for 2 hours and filtered to obtain a solid. The solid is dissolved in methylene chloride and the resultant organic solution is washed sequentially with 2N sodium hydroxide solution and brine, dried over anhydrous sodium sulfate and concentrated in vacuo to obtain a white solid. The white solid is recrystallized from hexanes to give the title product as white crystals (136 g, 91% yield).

As can be seen from the data in Example 2, the 4,6-difluoropyrimidine art process provides the title product in 40% yield starting from 4,6-dichloropyrimidine.

EXAMPLE 3

Preparation of 4-[(4-Chloro-α,α,α-trifluoro-m-tolyl)oxy]-6-[(α,α,α,4-tetrafluoro-m-tolyl)oxy]pyrimidine-4,6-Dichloropyrimidine Art Process a) Preparation of 4-Chloro-6-[(α,α,α,4-tetrafluoro-m-tolyl)oxy]pyrimidine

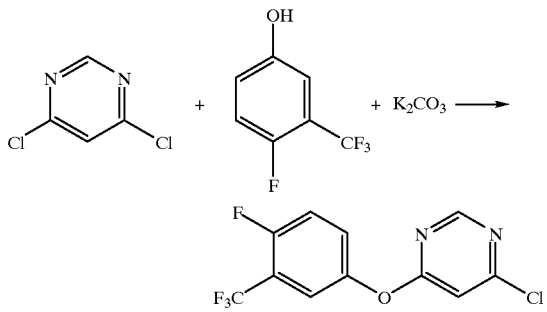

4-Chloro-6-[(α,α,α,4-tetrafluoro-m-tolyl)oxy]-pyrimidine is obtained in 99% yield according to the procedure described in Example 1.

b) Preparation of 4-[(4-Chloro-α,α,α-trifluoro-m-tolyl)oxy]-6-[(α,α,α,4-tetrafluoro-m-tolyl)oxy]pyrimidine

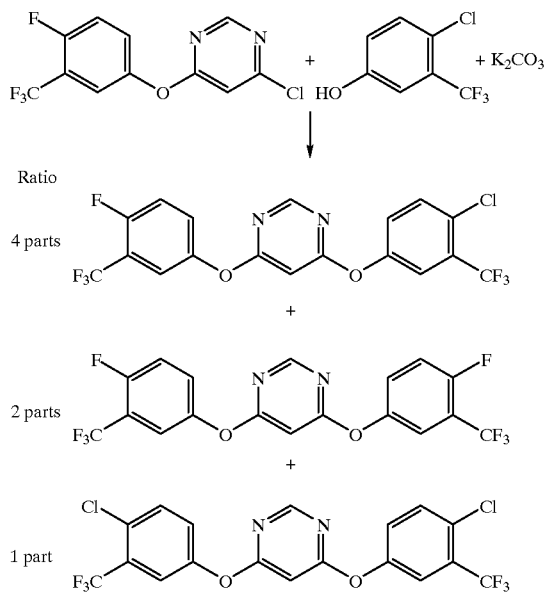

A solution of 4-chloro-6-[(α,α,α,4-tetrafluoro-m-tolyl)oxy]pyrimidine (0.25 g, 0.6 mmol), α,α,α-trifluoro-4-chloro-m-cresol (0.12 g, 0.6 mmol) and potassium carbonate (0.25 g, 1.8 mmol) in N,N-dimethylformamide is heated to and stirred at 60° C. for 24 hours, cooled and poured into water. The aqueous mixture is extracted with ether and the organic extract is washed with brine, dried over anhydrous magnesium sulfate and concentrated in vacuo to obtain a solid (0.21 g). The solid is found to contain the desired product and the two symmetrical compounds identified above in a 4:2:1 ratio by NMR analyses. It is difficult to separate the title compound from the symmetrical compounds and even before a separation is attempted, the title compound is only produced in about 30% yield.

Advantageously, the process of the present invention provides 4-[(4-chloro-α,α,α-trifluoro-m-tolyl)oxy]-6-[(α,α,α,4-tetrafluoro-m-tolyl)oxy]pyrimidine in significantly higher yield than the art processes (55% vs. 40% and 30%).

EXAMPLE 4

Preparation of 4-[(α,α,α-Trifluoro-4-nitro-m-tolyl)oxy]-6-[(α,α,α-trifluoro-m-tolyl)oxy]pyrimidine—Invention Process a) Preparation of 4-Chloro-6-[(α,α,α-trifluoro-m-tolyl)oxy]pyrimidine

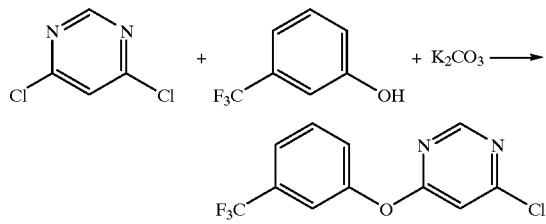

4,6-Dichloropyrimidine (14.9 g, 0.1 mol) is added to a mixture of m-trifluoromethylphenol (16.2 g, 0.1 mol) and potassium carbonate (14.5 g, 0.105 mol) in acetone (200 mL). The reaction mixture is stirred at room temperature for 2 days, refluxed for 3 hours, cooled and poured into water. The resultant aqueous mixture is extracted with methylene chloride. The organic extracts are combined, washed sequentially with 5% sodium hydroxide solution and water, dried over anhydrous magnesium sulfate and concentrated in vacuo to give the title product as an oil (27.4 g, 99% yield).

b) Preparation of Trimethyl{6-[(α,α,α-trifluoro-m-tolyl)oxy]-4-pyrimidyl}ammonium chloride

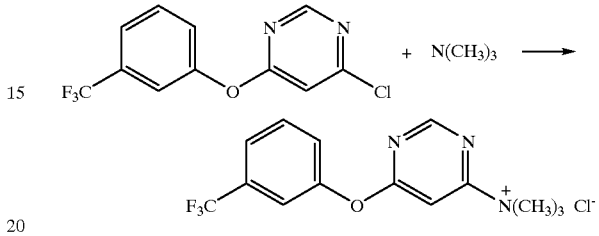

A trimethylamine/toluene solution (previously prepared by adding 27.4 mL of liquefied trimethylamine to toluene (325 mL) at 0° C.) is added to a solution of 4-chloro-6-[(α,α,α-trifluoro-m-tolyl)oxy]pyrimidine (27.4 g, 0.1 mol) in toluene (50 mL) over a 10 minute period. The reaction mixture is stirred overnight and filtered to obtain a solid. The solid is washed with hexane and dried overnight in a vacuum oven at 45–50° C. to give the title product as an off-white solid (23.3 g, 70% yield).

c) Preparation of 4-[(α,α,α-Trifluoro-4-nitro-m-tolyl)oxy]-6-[(α,α,α-trifluoro-m-tolyl)oxy]pyrimidine

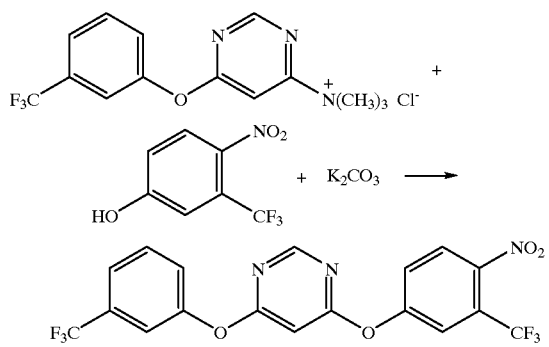

Trimethyl{6-[(α,α,α-trifluoro-m-tolyl)oxy]-4-pyrimidyl}ammonium chloride (22.8 g, 0.068 mol) is added to a mixture of α,α,α-trifluoro-4-nitro-m-cresol (15.1 g, 0.073 mol) and potassium carbonate (11.3 g, 0.082 mol) in N,N-dimethylformamide (125 mL). The reaction mixture is stirred at room temperature overnight and poured into water. The resultant aqueous mixture is extracted with methylene chloride. The organic extracts are combined, washed sequentially with 5% sodium hydroxide solution, water, 6N hydrochloric acid and water, dried over anhydrous magnesium sulfate and concentrated in vacuo to obtain a yellow solid. The solid is recrystallized from a 20:1 heptane/ethyl acetate solution to give the title product as an off-white solid (28.2 g, 93% yield).

As can be seen from the data in Example 4, the process of the present invention provides the title product in 64% yield starting from 4,6-dichloropyrimidine.

EXAMPLE 5

Preparation of 4-[(α,α,α-Trifluoro-4-nitro-m-tolyl)oxy]-6-[(α,α,α-trifluoro-m-tolyl)oxy]pyrimidine-4,6-Difluoropyrimidine Art Process a) Preparation of 4,6-Difluoropyrimidine

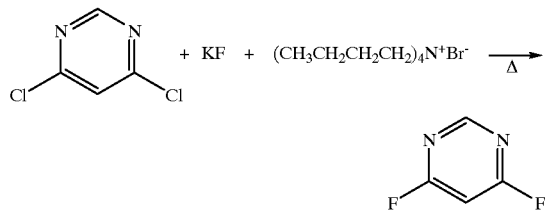

A mixture of 4,6-dichloropyrimidine (223.5 g, 1.5 mol), potassium fluoride (279.6 g, 4.8 mol) and tetrabutylammonium bromide (6.0 g, 0.0186 mol) in sulfolane (1 L) is heated at 180–190° C. for 3.5 hours and distilled to give the title product as a white liquid (115 g, 66% yield).

b) Preparation of 4-Fluoro-6-[(α,α,α-trifluoro-m-tolyl)oxy]pyrimidine

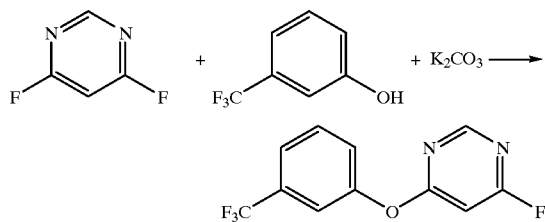

A solution of m-trifluoromethylphenol (74.5 g, 0.46 mol) in tetrahydrofuran (300 mL) is added dropwise to a mixture of 4,6-difluoropyrimidine (53.8 g, 0.46 mol) and potassium carbonate (60 g, 0.43 mol) in tetrahydrofuran (700 mL). The reaction mixture is stirred at room temperature for 3 days and poured into water. The resultant aqueous mixture is washed with 2N sodium hydroxide solution and extracted with ethyl acetate. The organic extract is dried over anhydrous magnesium sulfate and concentrated in vacuo to obtain a liquid. the liquid is vacuum distilled to give the title product as an oil (87.4 g, 74% yield).

c) Preparation of 4-[(α,α,α-Trifluoro-4-nitro-m-tolyl)oxy]-6-[(α,α,α-trifluoro-m-tolyl)oxy]pyrimidine

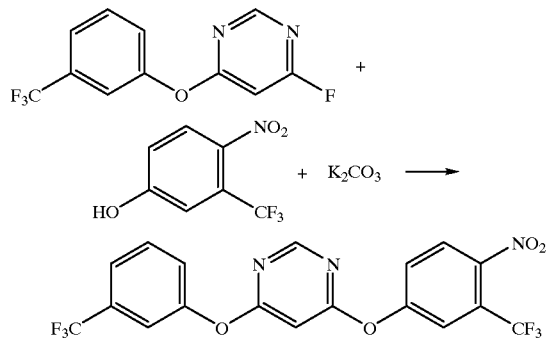

A mixture of 4-fluoro-6-[(α,α,α-trifluoro-m-tolyl)oxy]pyrimidine (87.4 g, 0.34 mol), α,α,α-trifluoro-4-nitro-m-cresol (84.9 g, 0.41 mol) and potassium carbonate (55 g, 0.40 mol) in N,N-dimethylformamide (1 L) is stirred at room temperature until the reaction is complete by thin layer chromatography analysis (8:1 hexanes/ethyl acetate). The reaction mixture is then poured into water and the resultant aqueous mixture is extracted with diethyl ether. The organic extract is dried over anhydrous magnesium sulfate and concentrated in vacuo to obtain a solid. The solid is recrystallized from an ethyl acetate/heptane solution to give the title product as a white solid (108 g, 71% yield).

As can be seen from the data in Example 5, the 4,6-difluoropyrimidine art process provides the title product in 35% yield starting from 4,6-dichloropyrimidine.

Advantageously, the process of the present invention provides 4-[(α,α,α-trifluoro-4-nitro-m-tolyl)oxy]-6-[(α,α,α-trifluoro-m-tolyl)oxy]pyrimidine in significantly higher yield than the art process (64% vs. 35%).

We claim:

1. A process for the preparation of an unsymmetrical 4,6-bis(aryloxy)pyrimidine compound having the structural formula

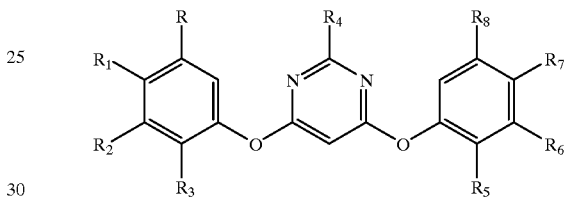

wherein

R and $R_8$ are each independently hydrogen or halogen;

$R_1$ and $R_7$ are each independently hydrogen, halogen, cyano, nitro, alkyl, trifluoromethyl, pentafluoroethyl, alkoxy, alkylthio, amino, alkylamino, dialkylamino, alkoxyalkyl, haloalkoxyalkyl or alkoxycarbonyl;

$R_2$ and $R_3$ are each independently hydrogen, halogen, alkyl, trifluoromethyl, pentafluoroethyl, haloalkoxy, haloalkenyl, haloalkynyl, haloalkoxyalkyl, alkoxycarbonyl, haloalkoxycarbonyl, haloalkylsulfinyl, haloalkylsulfonyl, nitro or cyano;

$R_3$ and $R_5$ are each independently hydrogen, halogen, alkyl or alkoxy; and $R_4$ is hydrogen, cyano, alkyl, alkoxy, alkylthio, alkylsulfinyl or phenyl;

provided that at least one of $R_2$ and $R_6$ is other than hydrogen, and that the aryloxy groups are not the same; which comprises reacting a 4,6-dihalopyrimidine compound having the structural formula

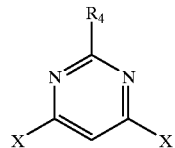

wherein $R_4$ is as described above and X is Cl, Br or I with one molar equivalent or less of a first phenol compound having the structural formula

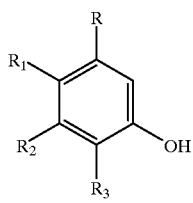

wherein R, $R_1$, $R_2$ and $R_3$ are as described above and a first base in the presence of a first solvent to form a 4-halo-6-(aryloxy)pyrimidine compound having the structural formula

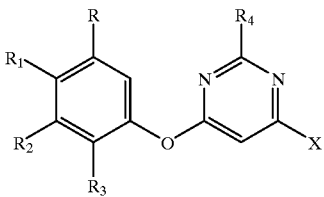

wherein R, $R_1$, $R_2$, $R_3$, $R_4$ and X are as described above, reacting the 4-halo-6-(aryloxy)pyrimidine compound with at least about one molar equivalent of a $C_1$–$C_4$trialkylamine, a 5- to 6-membered saturated or 5- to 14-membered unsaturated heterocyclic amine optionally substituted with one to three $C_1$–$C_4$alkyl groups or $C_1$–$C_4$alkoxy groups in the presence of a second solvent to form an ammonium halide compound having the structural formula

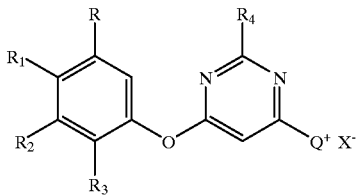

wherein R, $R_1$, $R_2$, $R_3$, $R_4$ and X are as described above, $Q^+$ is

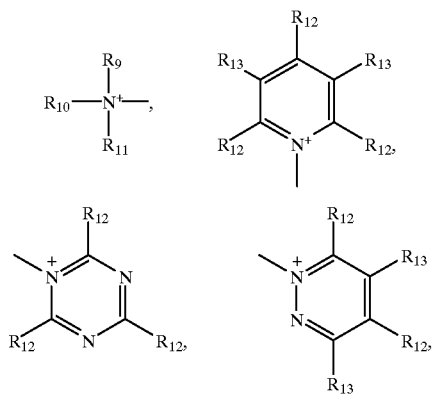

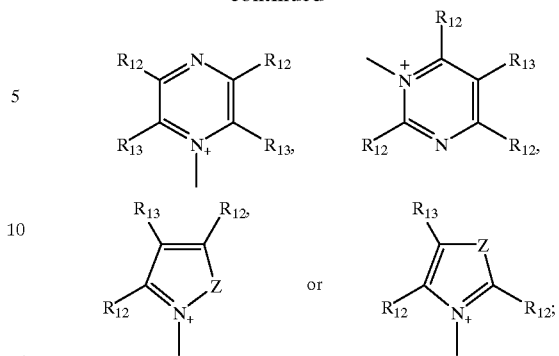

$R_9$, $R_{10}$ and $R_{11}$ are each independently $C_1$–$C_4$alkyl, and when taken together, $R_9$ and $R_{10}$ may form a 5- or 6-membered ring in which $R_9R_{10}$ is represented by the structure: —$(CH_2)_n$—, optionally interrupted by O, S or $NR_{14}$, where n is an integer of 3, 4 or 5, provided $R_{11}$ is $C_1$–$C_4$alkyl;

Z is O, S or $NR_{14}$, $R_{12}$ and $R_{13}$ are each independently hydrogen, $C_1$–$C_4$alkyl or $C_1$–$C_4$alkoxy, and when taken together, $R_{12}$ and $R_{13}$ may form a 5- or 6-membered saturated or unsaturated ring optionally interrupted by O, S or $NR_{14}$ and optionally substituted with one to three $C_1$–$C_4$alkyl groups or $C_1$–$C_4$alkoxy groups; and $R_{14}$ is $C_1$–$C_4$alkyl; and reacting the ammonium halide compound with at least about one molar equivalent of a second phenol compound having the structural formula

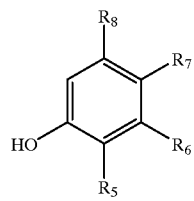

wherein $R_5$, $R_6$, $R_7$ and $R_8$ are as described above and a second base in the presence of a third solvent.

2. The process according to claim 1 wherein the first and second bases are selected from the group consisting of an alkali metal carbonate, an alkaline earth metal carbonate, an alkali metal hydride, an alkali metal hydroxide and an alkaline earth metal hydroxide.

3. The process according to claim 2 wherein the first and second bases are an alkali metal carbonate.

4. The process according to claim 1 wherein the first solvent is selected from the group consisting of an ether, a carboxylic acid amide, a halogenated hydrocarbon, a sulfoxide and a ketone; the second solvent is selected from the group consisting of an aromatic hydrocarbon and a chlorinated aromatic hydrocarbon; and the third solvent is selected from the group consisting of a carboxylic acid amide and a sulfoxide.

5. The process according to claim 4 wherein the first solvent is selected from the group consisting of a carboxylic acid amide and a ketone, the second solvent is an aromatic hydrocarbon, and the third solvent is a carboxylic acid amide.

6. The process according to claim 1 wherein X is Cl.

7. The process according to claim 1 wherein $Q^+$ is

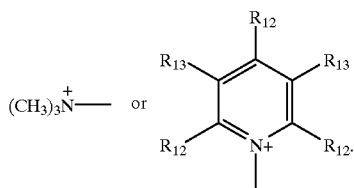

8. The process according to claim 7 wherein $Q^+$ is $(CH_3)_3N^+$—.

9. The process according to claim 1 wherein the 4,6-dihalopyrimidine compound is reacted with the first phenol compound and the first base at a temperature of about 0° C. to 100° C., the 4-halo-6-(aryloxy)pyrimidine compound is reacted with the amine at a temperature of about 0° C. to 100° C., and the ammonium halide compound is reacted with the second phenol compound and the second base at a temperature of about 0° C. to 100° C.

10. The process according to claim 1 wherein

R and $R_8$ are the same and each represents hydrogen or fluorine;

$R_1$ and $R_7$ are each independently hydrogen, halogen, cyano, nitro or $C_1$–$C_4$alkyl;

$R_2$ and $R_6$ are each independently hydrogen, fluorine, chlorine, $C_1$–$C_4$alkyl, trifluoromethyl, pentafluoroethyl, $C_1$–$C_4$haloalkoxy, $C_2$–$C_4$haloalkenyl, $C_1$–$C_4$alkoxycarbonyl or nitro;

$R_3$ and $R_5$ are each independently hydrogen, halogen or $C_1$–$C_4$alkyl; and $R_4$ is hydrogen, $C_1$–$C_4$alkylthio, $C_1$–$C_4$alkylsulfinyl or phenyl.

11. The process according to claim 10 wherein

R, $R_3$, $R_4$, $R_5$, and $R_8$ are hydrogen;

one of $R_1$ and $R_7$ is hydrogen, chlorine or cyano and the other is fluorine; and $R_2$ and $R_6$ are trifluoromethyl.

* * * * *